United States Patent
Vija et al.

(10) Patent No.: US 8,350,222 B2
(45) Date of Patent: Jan. 8, 2013

(54) MULTIMODALITY IMAGING

(75) Inventors: Alexander Hans Vija, Evanston, IL (US); Steffen Kappler, Effeltrich (DE); Guenter Hahn, Barrington, IL (US)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/939,036

(22) Filed: Nov. 3, 2010

(65) Prior Publication Data

US 2011/0089327 A1  Apr. 21, 2011

Related U.S. Application Data

(63) Continuation-in-part of application No. 12/503,963, filed on Jul. 16, 2009, now Pat. No. 7,863,574.

(60) Provisional application No. 61/257,511, filed on Nov. 3, 2009.

(51) Int. Cl.
*G01T 1/164* (2006.01)

(52) U.S. Cl. .............................. 250/363.05

(58) Field of Classification Search .. 250/363.01–363.1, 250/370.01–370.15; 378/98.8
See application file for complete search history.

(56) References Cited

U.S. PATENT DOCUMENTS

| | | | | |
|---|---|---|---|---|
| 4,937,453 | A | * | 6/1990 | Nelson ................. 250/370.09 |
| 7,697,659 | B2 | * | 4/2010 | Hoffman et al. ............... 378/19 |
| 7,863,574 | B2 | * | 1/2011 | Hahn et al. ............... 250/363.05 |
| 2005/0157839 | A1 | * | 7/2005 | Altman ........................ 378/4 |
| 2008/0001089 | A1 | * | 1/2008 | Lusser ................... 250/363.02 |

OTHER PUBLICATIONS

Saoudi et al., "A novel APD-based detector module for mutli-modality PET/SPECT/CT scanners," 1999, IEEE Transactions on Nuclear Science, vol. 46, No. 3, pp. 479-484.*

Iwata et al., "Description of a prototype combined CT-SPECT system with a single CZT detector," 2000, IEEE Nuclear Science Symposium Conference Record, vol. 3, pp. 16-1 to 16-5.*

* cited by examiner

*Primary Examiner* — Kiho Kim
(74) *Attorney, Agent, or Firm* — Peter Kendall

(57) ABSTRACT

An imaging system includes interleaved emission detectors and transmission detectors. Emission detectors and transmission detectors can be interleaved along the axis of relative patient motion. Emission detectors and transmission detectors can be interleaved orthogonal to the axis of relative patient motion. Emission detectors can be single photon emission computed tomography detectors and the transmission detectors can be x-ray computed tomography detectors.

16 Claims, 5 Drawing Sheets

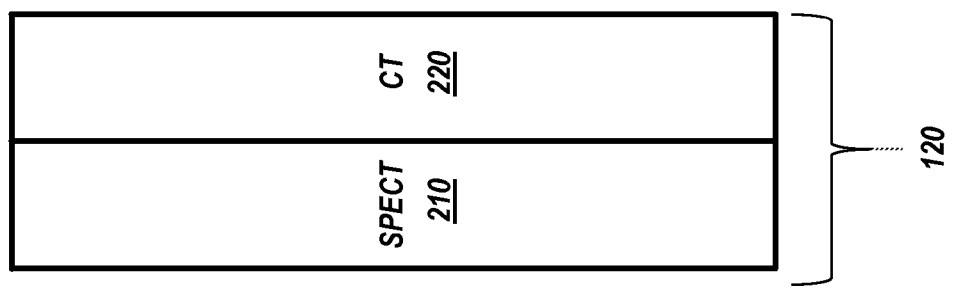
FIG. 2
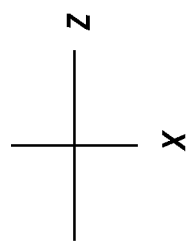

MULTIMODALITY IMAGING

CROSS REFERENCE TO RELATED APPLICATIONS

This application is a continuation-in-part of copending prior U.S. patent application Ser. No. 12/503,963, filed Jul. 16, 2009. This application also claims the benefit of U.S. Provisional Patent Application No. 61/257,511, filed Nov. 3, 2009.

FIELD

The technology disclosed herein (the "technology") relates to medical imaging, and in particular to multimodality medical imaging, e.g., combining a Single Photon Emission Computer Tomography (SPECT) and an X-ray Computer Tomography (CT).

BRIEF DESCRIPTION OF THE DRAWINGS

Reference will now be made, by way of example, to the accompanying drawings which show example implementations of the present application.

FIG. 2 illustrates a notional set of detectors for transmission radiation and emission radiation of the technology when viewed from the axis shown as X in FIG. 1. The axis of relative motion of a patient and patient handling system is shown as Z.

DETAILED DESCRIPTION

Figure 1:
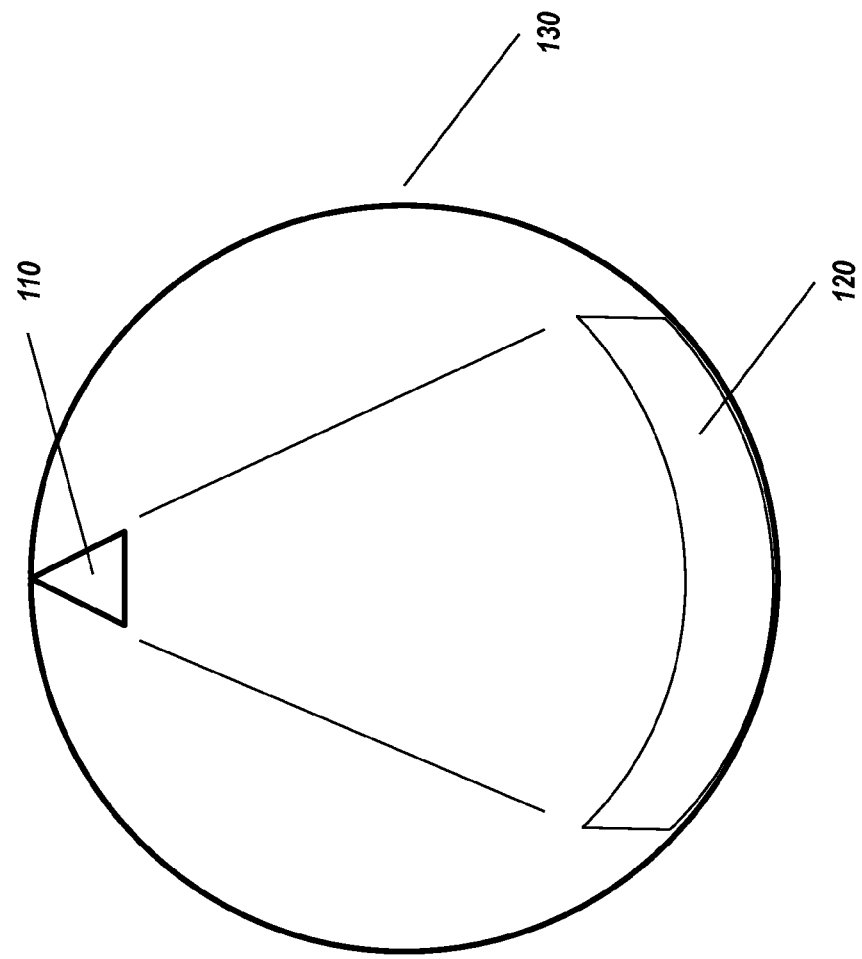
FIG. 1 illustrates a notional gantry of the technology containing an transmission source and detectors for transmission radiation and emission radiation. The axis Z of relative motion of a patient and patient handling system is substantially orthogonal to the plane of the figure.
Figure 1:
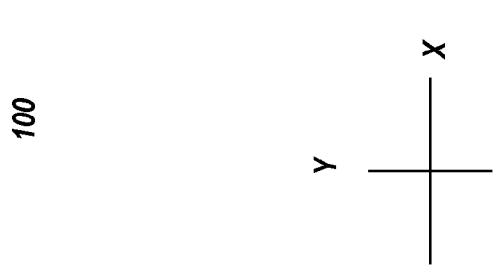

Reference will now be made in detail to implementations of the technology. Each example is provided by way of explanation of the technology only, not as a limitation of the technology. It will be apparent to those skilled in the art that various modifications and variations can be made in the present technology without departing from the scope or spirit of the technology. For instance, features described as part of one implementation can be used on another implementation to yield a still further implementation. Thus, it is intended that the present technology cover such modifications and variations that come within the scope of the technology.

Medical imaging technology may be used to create images of the human body for clinical purposes (e.g., medical procedures seeking to reveal, diagnose or examine disease) or medical science (including the study of normal anatomy and physiology). Medical imaging technology includes: radiography including x-rays, fluoroscopy, and x-ray computed axial tomography (CAT or CT); magnetic resonance imaging (MRI); and nuclear medical imaging such as scintigraphy using a gamma camera, single photon emission computed tomography (SPECT), and positron emission tomography (PET).

Computed tomography (CT) is a medical imaging method employing tomography created by computer processing. Digital geometry processing is used to generate a three-dimensional image of the inside of an object from a large series of two-dimensional X-ray images taken around a single axis of rotation. CT produces a volume of data which can be manipulated, through a process known as "windowing", in order to demonstrate various bodily structures based on their ability to block the X-ray beam. Although historically the images generated were in the axial or transverse plane, orthogonal to the long axis of the body, modern scanners allow this volume of data to be reformatted in various planes or even as volumetric (3D) representations of structures.

In nuclear medical imaging radiation can be used to acquire images that can show the function and anatomy of organs, bones or tissues of the body. The technique of acquiring nuclear medicine images entails first introducing radiopharmaceuticals into the body—either by injection or ingestion. These radiopharmaceuticals are attracted to specific organs, bones or tissues of interest. The exemplary organs, bones, or tissues are also more generally referred to herein using the term "objects". Upon arriving at their specified area of interest, the radiopharmaceuticals produce gamma photon emissions that emanate from the body that can be captured by a scintillation crystal. The interaction of the gamma photons with the scintillation crystal produces flashes of light which are referred to as "events." Events can be detected by an array of photo detectors (such as photomultiplier tubes) and their spatial locations or positions are then calculated and stored. In this way, an image of the organ or tissue under study can be created from detection of the distribution of the radioisotopes in the body.

In medical imaging so-called "hybrid modalities" are becoming increasingly important, for example PET-CT, SPECT-CT, PET-MRI and SPECT-MRI. One potential advantage of these combinations is the connection of a modality with a high local resolution (especially MRI or CT) to a modality with high sensitivity (especially SPECT or PET).

Various SPECT/CT systems are today commercially available. Typically, they consist of a SPECT and at CT system which are physically independent units, mounted together in more or less close proximity of each other, sharing one common patient bed, and sometimes a common cover. The separation is typically because of the different acquisition needs to form an image in these two modalities. For instance the currently used SPECT of a SPECT/CT either rotates slowly (T>>1 sec., e,g. Siemens Symbia T series, GE Infinia Hawkeye, Philips Brightview), or not at all using a stationary or quasi-stationary SPECT, e.g. GE's Discovery 570c, or Spectrum Dynamic's UltraFastSPECT.

SPEC/CT systems where the SPECT and CT components are separately mounted on the gantry have been proposed, e.g., in U.S. patent application Ser. No. 12/503,963, the disclosure of which is hereby incorporated herein by reference. The present disclosure discloses combined SPECT/CT detectors rotating about the patient opposite to an x-ray tube assembly on the same gantry. Such an approach not only provides tomographically consistent 4D SPECT acquisition, as well as 4D CT acquisition but also provides simultaneous or quasi-simultaneous 4D SPECT/CT acquisition of a common field of view (FOV).

Advantages of such an approach include smaller footprint than many other proposed SPECT/CT systems. Existing SPECT/CT systems use SPECT detectors and CT detectors that can be incompatible and thus independent structures supported by different gantries in close proximity sharing a common patient bed were used. Such systems present a large footprint, can be costly, and do not readily provide for near-simultaneous 4D SPECT/CT imaging. Systems of the present technology can provide simultaneous and near-simultaneous 4D SPECT/CT system with both the SPECT and CT images in 4D (3 spatial dimensions plus time) with a common field of view (FOV).

Implementations of the technology include solid state detectors for SPECT acquisition, both direct and indirect converters, e.g., cadmium zinc telluride (CZT), CdT, Silicon Photomultiplier (PM) (SiPM) with any suitable scintillation crystals, e.g., scintillation crystals having intrinsic resolution <3.9 mm. Implementations also include tungsten SPECT collimators with collimation schemes such as generalized focusing and coded aperture schemes. Multi-modality reconstruction techniques, such as those described in copending patent application Ser. No. 12/369,176 filed Feb. 11, 2009 and published as U.S. Patent Publication No. 20100014733, Ser. No. 12/369,172 filed Feb. 11, 2009 and published as U.S. Patent Publication No. 20100014732, and Ser. No. 12/369,159 filed Feb. 11, 2009 and published as U.S. Patent Publication No. 20100014730—each of which is incorporated herein by reference in its entirety.

Referring to FIG. 1 a notional gantry 130 of the technology containing a transmission source 110 and detectors 120 for transmission radiation and emission radiation is shown. The axis Z of relative motion of a patient and patient handling system is substantially orthogonal to the plane of the figure. In SPECT/CT systems, the transmission source 110 can include an x-ray tube. The detectors 120 can be placed substantially opposite to the x-ray source, though other placements can be used with the use of collimators on the source 110, the detectors 120, or both. The gantry 110 is shown as a closed circle for simplicity. Other gantry configurations, including open and cantilever gantries can be used. Patient motion relative to the gantry 130 can be along the Z axis, e.g., in a periodic, iterative, shuttled, or unidirectional fashion.

Figure 3:
FIG. 3 illustrates a notional set of detectors for transmission radiation and emission radiation of the technology from the view of FIG. 2. The axis of relative motion of a patient and patient handling system is shown as Z.
Figure 3:
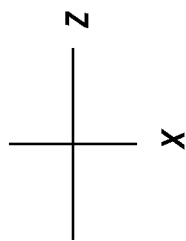
Figure 5:
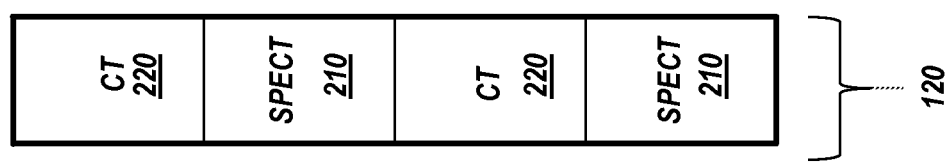
FIG. 5 illustrates a notional set of detectors for transmission radiation and emission radiation of the technology from the view of FIG. 2. The axis of relative motion of a patient and patient handling system is shown as Z.
Figure 5:
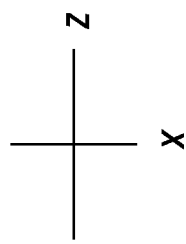

In implementations of the technology, emission detectors and transmission detectors are interleaved. FIG. 2, FIG. 3, and FIG. 5 show various relative geometries for interleaving emission detectors 210 and transmission detectors 220. Emission detectors are shown in the figures as SPECT detectors 210, and transmission detectors are shown as CT detectors 220, as examples. In FIG. 2, the overall detector array 120 is divided into a SPECT slice 210 and a CT slice 220. In FIG. 3, the array 120 includes alternating slices of CT detectors 220 and SPECT detectors 210. Implementations of the technology can include additional slices of each type of detector depending on the specific image performance desired, considering factors such as the speed of acquisition; which typically differs between slower emission detectors and faster transmission detectors. While FIG. 2 and FIG. 3 show detector slices alternating along Z axis, detector elements, e.g., emission detectors 510 and transmission detectors 520 can alternate along the direction of the gantry perimeter as shown in FIG. 5. Implementations of the technology can combine the interleaving approaches shown in FIG. 2, FIG. 3, and FIG. 5. The transmission detectors 220, 520 can be conventional CT detectors, or preferably photon (quantum) counting CT detectors.

Some implementations can enable material decomposition method, e.g., by using fast kV switching if a conventional CT detector is used or quantum counting CT detectors. In some implementations, emission list mode data is distributed from the emissions detectors using the transmission data distribution backbone.

The present technology can provide cost savings over existing approaches through use of less elements, e.g., transmission detectors and emission detectors can use the same mounting structures and data bus. Further, systems of the technology can be used for standalone diagnostic CT.

In some implementations, energy discrimination between transmission detection and emission detection is used to provide from concurrent to near simultaneous acquisition for transmission images (primarily structural/anatomical data) and emission images (primarily functional data). In such implementations, the maximum CT energy $E_{CTmax}$ can be less than the energy associated with nuclear medical imaging substances, e.g., technetium-99, thallium-201, and other clinical nuclear medicine isotopes.

Implementations of the technology can provide for direct determination of the μ map through fast kV switching. In those implementations the CT source is switched from a higher energy (e.g. 130 kV peak) to a lower energy (e.g., 80 kV peak) thereby measuring the response of the body to two different energies, allowing determination of the μ map directly.

The present technology can take the forms of hardware, software or both hardware and software elements. In some implementations, the technology is implemented in software, which includes but is not limited to firmware, resident software, microcode, a Field Programmable Gate Array (FPGA), graphics processing unit (GPU), or Application-Specific Integrated Circuit (ASIC), etc. In particular, for real-time or near real-time use, an FPGA or GPU implementation would be desirable.

Furthermore, portions of the present technology can take the form of a computer program product comprising program modules accessible from computer-usable or computer-readable medium storing program code for use by or in connection with one or more computers, processors, or instruction execution system. For the purposes of this description, a computer-usable or computer readable medium can be any apparatus that can contain, store, communicate, propagate, or transport the program for use by or in connection with the instruction execution system, apparatus, or device. The medium can be nontransitory (e.g., an electronic, magnetic, optical, electro-magnetic, infrared, or semiconductor system (or apparatus or device)) or transitory (e.g., a propagation medium). Examples of a nontransitory computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD. Both processors and program code for implementing each as aspect of the technology can be centralized or distributed (or a combination thereof) as known to those skilled in the art.

Figure 4:
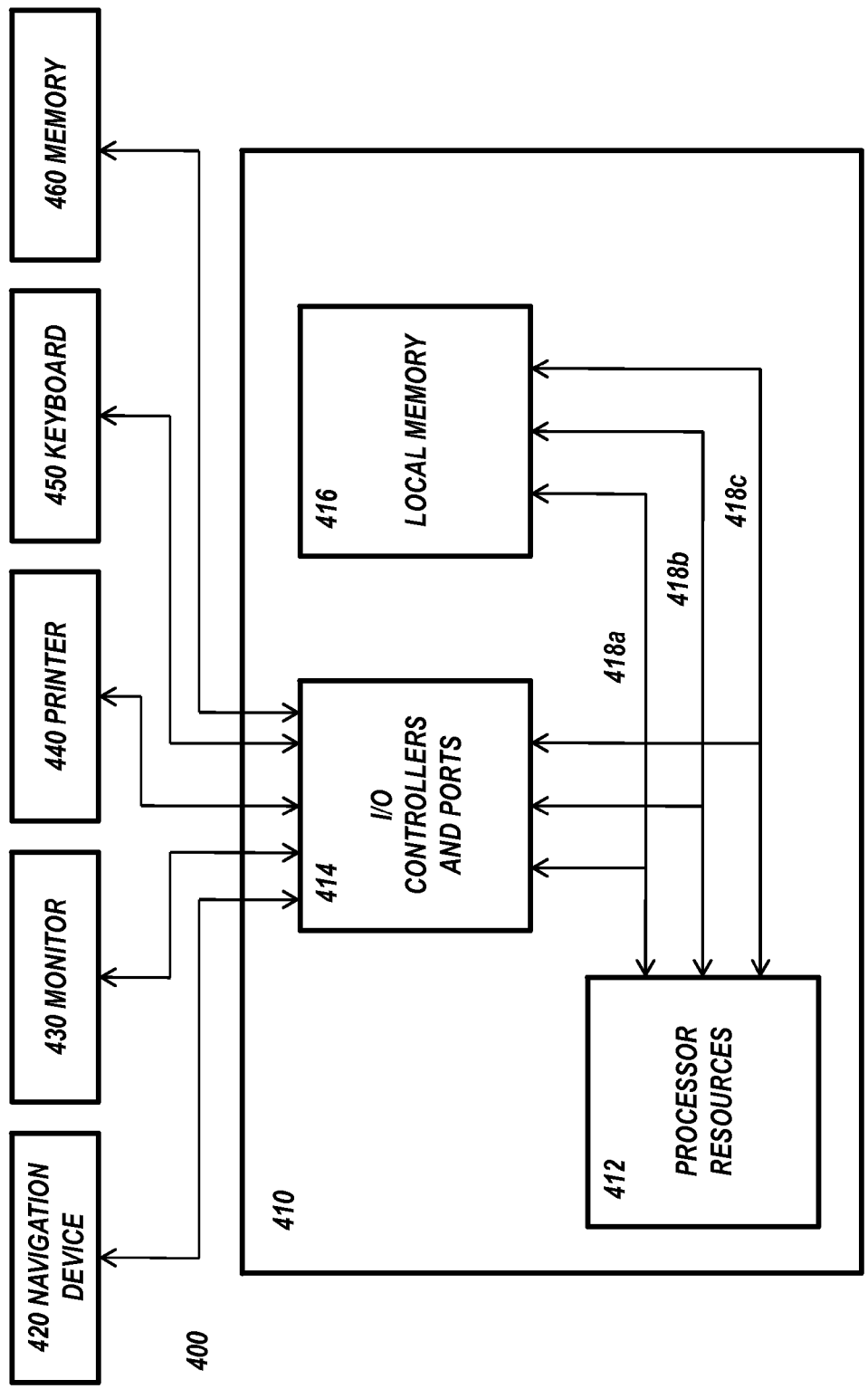
FIG. 4 illustrates a data processing system suitable for storing a computer program product of the present technology.

Referring to FIG. 4, a data processing system (e.g., 400) suitable for storing a computer program product of the present technology and for executing the program code of the computer program product can include at least one processor (e.g., processor resources 412) coupled directly or indirectly to memory elements through a system bus (e.g., 418 comprising data bus 418a, address bus 418b, and control bus 418c). The memory elements can include local memory (e.g., 416) employed during actual execution of the program code, bulk storage (e.g., 460), and cache memories (e.g., including cache memory as part of local memory or integrated into processor resources) that provide temporary storage of at least some program code in order to reduce the number of times code must be retrieved from bulk storage during execution. Input/output or I/O devices (including but not limited to keyboards 450, displays 430, pointing devices 420, etc.) can be coupled to the system either directly or through intervening I/O controllers (e.g., 414). Network adapters can also be coupled to the system to enable the data processing system to become coupled to other data processing systems or remote printers or storage devices through intervening private or public networks. Modems, cable modem and Ethernet cards are just a few of the currently available types of network adapters. Such systems can be centralized or distributed, e.g., in peer-to-peer and client/server configurations. In some implementations, the data processing system is implemented using one or both of FPGAs and ASICs.

The invention claimed is:

1. An imaging system comprising:
a gantry operable to rotate about a patient;
an x-ray source connected with the gantry such that the x-ray source rotates with the gantry; and
interleaved emission detectors and transmission detectors connected with the gantry such that the interleaved emission detectors and transmission detectors rotate with the gantry opposite to the x-ray source, the interleaving being spaced perpendicularly to a direction of incidence of radiation onto the emission and transmission detectors, wherein the emission detectors and the transmission detectors are separate, alternating types of detector units that abut perpendicularly to the direction.

2. The system of claim 1 wherein: the emission detectors and the transmission detectors are interleaved along the axis of relative patient motion.

3. The system of claim 1 wherein: the emission detectors and the transmission detectors are interleaved orthogonal to the axis of relative patient motion.

4. The system of claim 1 wherein: the emission detectors are single photon emission computed tomography detectors and the transmission detectors are x-ray computed tomography detectors.

5. The system of claim 4 wherein: the transmission detectors are photon counting detectors.

6. The system of claim 5 wherein: the photon counting detectors are fast kV switching photon counting detectors, and the maximum transmission energy is greater than the energy of the emission radiopharmaceutical.

7. The system of claim 4 wherein: the emission detectors and the transmission detectors share a data transmission backbone.

8. The system of claim 1 wherein: the emission detectors comprise converters other than scintillation crystals, and the transmission detectors comprise computed tomography detectors separate from the converters.

9. An imaging system comprising:
a gantry;
a radiation source connected with the gantry; and
emission detectors and transmission detectors connected with the gantry opposite the radiation source;
wherein the emission detectors and transmission detectors are physically independent units spatially interleaved such that the physically independent emission detectors and transmission detectors abut perpendicularly to a direction of incidence of the radiation from the radiation source onto the emission and transmission detectors.

10. The system of claim 9 wherein: the emission detectors comprise photomultiplier tubes and the transmission detectors comprise computed tomography detectors separate from the photomultiplier tubes.

11. The system of claim 9 wherein the emission detectors and the transmission detectors are mounted to rotate together with the gantry.

12. The system of claim 9 wherein the emission detectors and the transmission detectors are both positioned within a field of view of the radiation source.

13. The system of claim 9 wherein the emission detectors and the transmission detectors have a same mounting structure.

14. The system of claim 1 wherein the emission detectors and the transmission detectors have a same mounting structure.

15. The system of claim 1 wherein the emission detectors and the transmission detectors abut.

16. The system of claim 1 wherein the emission detectors and the transmission detectors are both in a field of view of the radiation source.

* * * * *